United States Patent

Bernard et al.

Patent Number: 5,250,419
Date of Patent: Oct. 5, 1993

[54] METHOD FOR THE DIRECT MEASUREMENT OF AT LEAST ONE CHEMICAL PARAMETER OF SKIN USING A BIOSENSOR

[75] Inventors: Dominique Bernard, Compiegne; Michel Kermici; Michel Prunieras, both of Paris, all of France

[73] Assignee: L'Oreal, Paris, France

[21] Appl. No.: 744,382

[22] Filed: Aug. 13, 1991

Related U.S. Application Data

[62] Division of Ser. No. 450,812, Dec. 14, 1989, abandoned.

[30] Foreign Application Priority Data

Dec. 16, 1988 [FR] France ............... 88 16664

[51] Int. Cl.$^5$ .......... C12Q 1/00; A61B 5/00; C12M 1/40; C12M 1/34
[52] U.S. Cl. ............ 435/25; 435/4; 435/291; 435/288; 435/817; 204/153.12; 204/403; 128/635
[58] Field of Search ........... 435/291, 288, 817, 4, 435/125; 204/153.12, 153.17, 402, 3, 415; 128/632-639, 643; 604/355, 356, 289

[56] References Cited

U.S. PATENT DOCUMENTS

| | | | |
|---|---|---|---|
| 4,024,042 | 5/1977 | Enfors et al. | 204/195 |
| 4,071,020 | 1/1978 | Pugliese | 422/68.1 |
| 4,172,770 | 10/1979 | Semersky et al. | 435/291 |
| 4,458,686 | 7/1984 | Clark, Jr. | 128/635 |
| 4,488,557 | 12/1984 | Engel | 128/635 |
| 4,721,677 | 1/1988 | Clark, Jr. | 435/291 |
| 4,759,828 | 7/1988 | Young et al. | 204/403 |
| 4,985,125 | 1/1991 | Watanabe et al. | 204/415 |
| 5,050,604 | 9/1991 | Reshef et al. | 128/632 |

OTHER PUBLICATIONS

Durliat et al., "Reagentless Amperometric Lactate Electrode", Analytical Chemistry, 1980, 52, 2109.
Mizutani et al., "Sequential Determination of L-Lactate and Lactate Dehydrogenase w/Immobilized Enzyme Electrode", Analytical Chem., 1983, 55, 35.
Kernevez et al., "Determination of Substrate Concentrations by a Computerized Enzyme Electrode", Biotech. & Bioeng., 1983, 25, 845.
Mascini et al., "A Lactate Electrode With Lactate Oxidase immobilized on nylon net for Blood Serum Samples in flow Systems", Anal. Chem. Acta. 1984, 157,45.
Mullen et al., "Enzyme Electrode for the Measurement of Lactate in Undiluted Blood", Clin. Chem. Acta, 1986, 157, 191.

*Primary Examiner*—Robert J. Warden
*Assistant Examiner*—T. A. Trembley
*Attorney, Agent, or Firm*—Cushman, Darby & Cushman

[57] ABSTRACT

This biosensor comprises a membrane (8), in which an enzyme catalyzing the transformation of a substrate used in the cutaneous metabolism is immobilized, means for detecting and measuring a phenomenon caused by said transformation, which is representative of the concentration of the substrate to be measured, with said substrate being brought into contact with the enzymatic membrane (8), and a measuring cell (13), a wall area of which is formed by the membrane (8) and which is capable of being closed, during the measurement, by a cutaneous covering area (15), with the cell (13) being combined with means for making circulate therein a liquid for placing in solution the substrate to be measured. For the measurement, the biosensor is applied to the skin, the buffer is injected into the cell and, once said cell is filled, the detection and the measurement are carried out, then the buffer is again made to circulate in order to remove the solubilized substrate. This measuring cycle can be repeated without removing the electrode (1). The biosensor is used for measurement of cutaneous L-lactate with a Clark electrode combined with a membrane using L-lactate oxidase.

4 Claims, 7 Drawing Sheets

METHOD FOR THE DIRECT MEASUREMENT OF AT LEAST ONE CHEMICAL PARAMETER OF SKIN USING A BIOSENSOR

This is a division of application Ser. No. 07/450,812, filed Dec. 14, 1989, now abandoned.

BACKGROUND OF THE INVENTION

The present invention relates to an enzyme biosensor intended for the direct measurement of biochemical parameters of the skin, as well as to the corresponding method of measurement and the method for preparation of the necessary enzymatic membrane.

A large number of techniques are known for the in vivo measurement, in a non-invasive manner, of physical parameters of the skin. While considerable data is available on these physical parameters, few, however, are available about the biological signals which are directly accessible on the *stratum corneum*, and methods for measurement providing the direct acquisition of such signals are practically non-existent at the present time.

These biochemical factors are, however, interesting from a diagnostic point of view. Thus, for example, the energetic metabolism of the skin comprises a preponderant anaerobic cycle with formation of tactic acid from pyruvic acid; this lactic acid is found in the suprabasal layers of the epidermis, as well as in the *stratum corneum*. One of the roles described for the exogenous lactate is that of natural hydrating agent for the skin due to its hygroscopic properties (Van Scott et al, J. Am. Acad. Dermatol. 1984, 11. 869; and Takahashi et al., J. Soc. Cosmet. Chem. 1985, 36, 177). In addition, it is known that an increase in the amount of lactate is a sign of cell hyperproliferation in the deep layers.

The interest of a device providing, under the best conditions, a measurement of the lactate on the skin would, in particular, therefore, be to be able to determine the importance of this metabolite on the hydration of the skin and its possible diagnostic or curative role. The best conditions, of which it is question, are those of direct measurement, without a sampling step and without placing a reagent on the skin. In addition, it could be interesting to be able to carry out repeated measurements on a same site, for example, at one minute intervals, so as to observe phenomena of exhaustion or of facilitated diffusion of the cutaneous lactate.

In reality, it would be generally useful to have means for direct measurement on the cutaneous coating of all dermatologically or cosmetically interesting molecules, such as, for example, urea, cholesterol or amino acids. The studies to be carried out can further, also in a general manner, relate to the remanence, the absorption and the release of one of the compounds in question.

However, taking lactate as an example, the normal methods for determination of this substance, outside of the fact of requiring a sampling step, are sensitive but relatively slow (Barker et al., J. Biol. Chem. 1941, 138, 535). The same disadvantages can be attributed to the enzymatic method using dehydrogenase lactate, hereinafter called LDH (E.C. 1.1.1.27), which is based on the detection at 340 nm of the coenzyme, nicotinamide-adenine-reduced dinucleotide; moreover, interference related to the presence of LDH effecters in the sample can be detrimental to the sensitivity of the measurement (Gutman et al., in H.U. Berymeyer (Ed.), Methods of Enzymatic Analysis, Verlag Chemie, Weinham, 2nd Edition 1974, 264).

In addition, the electrochemical sensors, combined with a film, in which an enzyme is immobilized, have already been widely used to determine compounds found in biological media. Thus, there exists at the present time a large number of L-lactate specific enzymatic electrodes which are used in the field of agro-food industries, as well as in that of medical analyses. Enzyme electrodes using one of four enzymatic systems which can be envisaged for such applications have been described:

LDH [Durliatt et al. Anal. Chem. 1980,52, 2109];

cytochrome b2 (E.C. 1.1.2.3) [Shinbo et al. Anal. Chem. 1979, 51, 100];

2-mono-oxygenase lactate (E.C.1.13.12.4) of Mycobacterium smegmatis which catalyzes the following reaction:

combined with a Clark electrode [Mascini et al. Anal. Chem. Acta 1984, 157, 45];

oxidase lactate (E.C.1.1.3.2) of Pediococcus sp., with which the best results are obtained from the point of view of stability, of sensitivity and of reliability and which catalyzes the following reaction:

L-lactate+$O_2$→pyruvate+$H_2O_2$ combined with detection of the partial oxygen pressure [Mizutani et al. Anal. Chem. 1983, 55, 35] or with detection of $H_2O_2$ [Mullen et al. Clin. Chem. Acta 1986, 157, 191].

In order to achieve the objective indicated above, which is that of being able to determine, through direct measurements, the biochemical parameters of the skin, it was interesting to use the known method in accordance with which the sample to be measured was brought into contact with a membrane in which an enzyme is immobilized (as described by Romette, Doctoral Thesis, University of Compiegne, 1986), which enzyme will catalyze the transformation of the substance to be measured with, particularly in the case of L-lactate, oxygen consumption and production of $H_2O_2$, with means being provided to detect a phenomenon caused by the consumption of oxygen or the production of $H_2O_2$, for example means for amperometric detection of the decrease in partial oxygen pressure (one example being the Clark electrode which is described in more detail below), with the enzymatic membrane being applied to the sensitive end of the electrode.

In effect, the sensitivity of such biosensors is most often considerable. However, the direct application of the electrode on the cutaneous surface has been shown to be impossible, due to difficulties arising from the compression of the electrolyte film, the mechanical resistance of the membrane and the placing in solution of the substrate.

SUMMARY OF THE INVENTION

The applicants have overcome these disadvantages by combining with an enzyme biosensor of the above-identified type a cell for placing in solution the substrate to be measured, in which a suitable liquid medium, such as a buffer, can be made to circulate, with said cell comprising an opening which, in the measuring position, is blocked by a cutaneous covering zone, which constitutes the measurement site.

It also follows from the placing of this cell with fluid circulation, which is closed by an area of skin at the moment of measurement, that the injection of the measuring buffer can be made automatic, and especially that several measuring cycles can be carried out on a same site, which corresponds to one of the important objectives indicated above.

DETAILED DESCRIPTION OF THE INVENTION

The object of the present invention is therefore firstly an enzyme biosensor intended for the direct measurement of at least one biochemical parameter of the skin, with said biosensor comprising, on the one hand, a membrane, in which an enzyme intended to catalyze the transformation of a substrate used in the cutaneous metabolism is immobilized, and, on the other hand, means for detecting and measuring a phenomenon caused by said transformation, which is representative of the concentration of the substrate to be measured, with said substrate being brought into contact with the enzymatic membrane, characterized by the fact that it comprises a measuring cell containing an opening, with a wall area of said cell being composed of said enzymatic membrane and wherein the above-identified opening is capable of being closed, during the measurement, by a cutaneous covering area, with said cell being combined with means for making circulate a liquid for placing in solution the substrate to be measured.

In such a system of direct measurement, the result obtained is the reflection, on the one hand, of the concentration of the cutaneous substrate, which it is desired to measure, and on the other hand, constraints of diffusion which the skin can set against the diffusion of this substrate to the measuring cell, with said constraints of diffusion capable of being related to the type of skin.

In a preferred embodiment, in accordance with which the transformation of the substrate to be measured is a reaction which consumes oxygen and/or produced $H_2O_2$, the means for detection and measurement are composed of an electrode measuring the decrease in the partial oxygen pressure or the increase in the concentration of $H_2O_2$, with the enzymatic membrane being applied against the sensitive part of the end of said electrode, and with the liquid for placing in solution being a buffer capable of supplying oxygen; the measuring cell is preferably composed of a ring, at the end of which is sealably mounted the sensitive end part of said electrode, with the other end of said ring comprising the opening of the cell.

In the biosensor of the invention, the enzymatic membrane can preferably be composed of a film-support of hydrophobic material with selective permeability with regard to gases and of a film carrying the enzyme formed by crosslinking at least one inert protein with a bridging agent, such as glutaraldehyde; the film-support of the enzymatic membrane is arranged on the side of the electrode and the film carrying the enzyme is arranged opposite the opening of the measuring cell.

Particular mention can be made of a biosensor in accordance with the invention intended for the measurement of cutaneous L-lactate, with the enzyme being L-lactate oxidase, in particular Pediococcus sp. L-lactate oxidase and the electrode being an electrode measuring the decrease in the partial oxygen pressure (so-called Clark electrode); the film carrying the enzyme contains from 0.15 to 0.50 International Units (IU) of L-lactate oxidase per $cm^2$ of membrane. This thickness of the carrier film is preferably between 30 and 50 $\mu m$; the inert protein is, for example, gelatin.

In the particular case indicated, the constituent hydrophobic material of the film-support is, preferably, polypropylene or polytetrafluoroethylene. The thickness of the film-support is preferably between 6 and 15 $\mu m$.

For the preparation of an enzymatic membrane intended for a biosensor in accordance with the invention intended for the measurement of L-lactate, the following steps are followed:

a) an aqueous solution i:% prepared containing, per ml, from 4 to 20 IU of L-lactate oxidase and from 30 to 70 mg of gelatin;

b) said solution is spread on a film-support at a rate of 10 to 50 $\mu m/cm^2$ and this coating is dried;

c) on the dried coating obtained, an aqueous solution of glutaraldehyde having a concentration of between 0.5 and 2% by weight is poured and allowed to crosslink for a time of between 1.5 and 4 minutes.

A further object of the present invention is a method for the direct measurement of at least one biochemical parameter of the skin using a biosensor such as defined above, wherein said biosensor is applied on selected area of cutaneous covering, such that the opening of the measuring cell is closed by said area of cutaneous covering; into said cell is injected a liquid capable of solubilizing the cutaneous substrate which it is sought to measure and the composition of which promotes catalysis; after filling the measuring cell, the detection and the measurement are carried out of the phenomenon caused by the transformation of the substrate due to the catalysis of the enzyme of the membrane; then the solubilization liquid of the substrate is made to circulate.

The above-indicated measuring cycle can preferably be repeated on the same site, in which case the enzymatic membrane is not exposed to air between two successive cycles.

Where the biosensor is intended to measure the cutaneous lactate by using lactate oxidase, it is preferable to use, as the liquid for placing the cutaneous lactate in solution, a buffer having a pH of between 6 and 8; that the variation in partial oxygen pressure $pO_2$ as a function of time during the period of non-circulation of the buffer in the cell be recorded; that on the recording the point A having for abscissa the beginning of the injection of the buffer and for ordinate the maximum value of $pO_2$ is defined; that the straight line D connecting A to the minimum B of the recorded curve is defined and the its slope P is measured in order to use it as a representative value of the amount of cutaneous lactate. In this type of measurement, the circulation of the buffer is preferably stopped for a time of between 3 and 6 minutes.

It is appropriate to point out that the biosensor in accordance with the invention can preferably be used in particular for the measurement of a parameter of cutaneous hydration and for the estimation of sudoral secretion. In the case of measuring a parameter of cutaneous hydration, the biosensor can be particularly useful in helping to diagnose the dryness of a skin. In the case of estimating the amount of sudoral secretion, the biosensor enables the evaluation of the effectiveness of perspiration-inhibiting products. These uses are based on the fact that the lactate is found in high concentrations in sudoral secretions (15 to 40 m/M), with the measurement of amounts of lactate therefore providing a direct estimation of the sudoral secretion.

BRIEF DESCRIPTION OF THE DRAWINGS

To understand more fully the object of the invention, the preparation of a biosensor for cutaneous use for the measurement of L-lactate is described below in more detail for purely illustrative and non-limiting purposes, with reference to the attached drawings.

In these drawings:

FIG. 1 represents a Clark electrode 1 of a known type, which is suitable, as a base element, for the preparation of an L-lactate biosensor in accordance with the invention, with a view to measuring cutaneous L-lactate. Electrode 1 comprises a body 3 housed in an envelope 4. The free end of the electrode 1 is covered with a hydrophobic film 5, which allows only oxygen to pass and which is, for example, a polypropylene or polytetrafluoroethylene film; this end of the electrode is protected by a tip 2 which, nevertheless, permits measurements. The fixing of the film 5 is shown in more detail on FIG. 1a, which shows, on an enlarged scale, the corresponding end part of electrode 1, without the tip 2. The envelope 4 of the electrode 1 contains, close to its end, an annular groove 6 intended to receive a toroidal joint 7, with interposition of film 5. Close to its end opposite film 5, the body 3 of the electrode 1 contains an annular shoulder 3a supported on a corresponding bearing surface 4a of envelope 4, with interposition of a joint 9; between said joint 9, the envelope 4 and the body 3 of the electrode 1, is provided a space filled with electrolyte 10, with the electrolyte 10 being interposed between the electrode 1 and the film 5. The envelope 4 further contains a lateral opening 11, with a view to carrying out a purge of the electrolyte and the balancing of the pressure of the electrolyte, with the opening 11 normally being sealably closed by a ring 2.

FIG. 2 shows in a schematic manner the end of the Clark electrode corresponding to FIGS. 1 and 1a as modified to prepare a biosensor in accordance with the invention. On said end, in accordance with the present invention, there has been adapted a measuring cell 13 with circulation, composed of a bottomless ring 14. The end of the electrode 1 is sealably arranged, by means of a joint 14a, to an end of said ring 14, the other end of which is intended to take support on the cutaneous surface 15 during measurement. The cell 13 is intended to be traversed by a flow of measuring buffer supplied through the entry tube 16 and removed through exit tube 17. This fluid circuit comprises means (not shown), such as a pump, ensuring the injection of the measuring buffer through tube 16.

Figure 1:
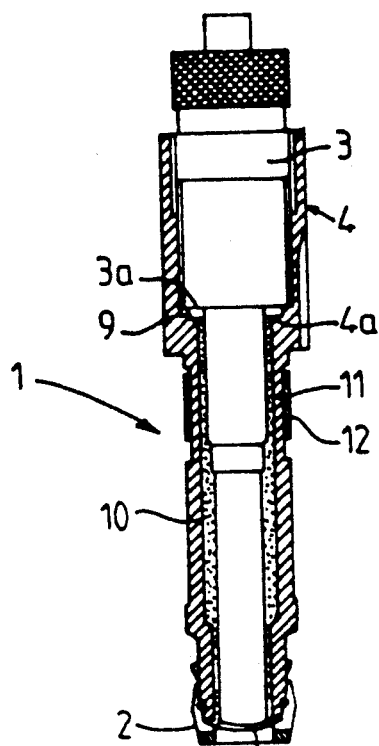
FIGS. 1, 1A and 2 relate to the electrode used.
Figure 1A:
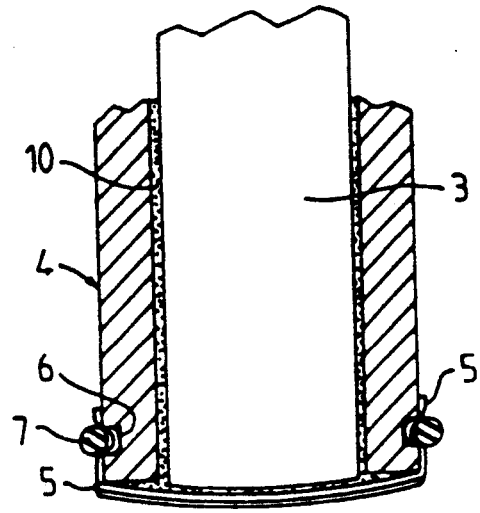

In order to prepare a biosensor in accordance with the invention, a suitable enzymatic membrane is first prepared, then a Clark electrode such as described above is equipped with the same. A precise example for these two steps is given below.

1) Production of the enzymatic membrane

A solution with 5% (weight/volume) of 250 bloom Chaulee ossein gelatin (Rousselot, France) in a phosphate buffer 0.02 M, pH 6.8 was prepared (this solution was kept for a maximum of one week at 4° C. before being used).

In its flask of 100IU (reference: Sigma, No. L-0638), the lyophilized Pediococcus Sp. L-lactate oxidase was solubilized with 500 μl of phosphate buffer 0.1 M, pH 7.1, and kept at 4° C. before being used.

A solution of 1.25% glutaraldehyde (weight/volume) in a phosphate buffer 0.02 M, pH 6.8, was prepared extemporaneously from quality 1 glutaraldehyde (Sigma No. G-5882) in an aqueous solution with 25% by weight.

The gelatin solution prepared in this manner was heated to 45° C. for 5 minutes. It was then cooled to 30° C. 1 ml of this solution was then removed and the mixture was homogenized with 50 μl of the enzymatic solution (10 IU). The homogenized mixture was poured onto a polypropylene (Bollore) film with a thickness of 6 μm fixed on a sheet of perfectly flat glass. The solution was spread over a surface of exactly 35 cm$^2$, defined by an adhesive strip. The application of a flow of air, at room temperature, for 40 minutes, ensured drying of the membrane.

The crosslinking of this membrane was then carried out with the glutaraldehyde solution, by applying 10 ml of same onto the membrane for exactly 3 minutes. Rinsing with 3 liters of distilled water was then carried with continuous flow on the membrane in order to stop the crosslinking and remove the excess of the bridging agent.

12 membranes were then able to be cut which were capable of being applied onto the Clark electrode being used. These were kept at 4° C. in a phosphate buffer 0.1 M, pH 7.1, until they were placed at the end of the electrode and used.

2) Preparation and use of the electrode with the enzyme

A Clark electrode was used (Radiometer, Copenhagen, Denmark, Model E 5046), as shown in FIG. 1. The oxygen-sensitive zone of this electrode was covered with an enzymatic membrane 8, as prepared in the preceding step, with the polypropylene film-support 5, which was gas-selective, being on the side of the electrode.

Figure 2:
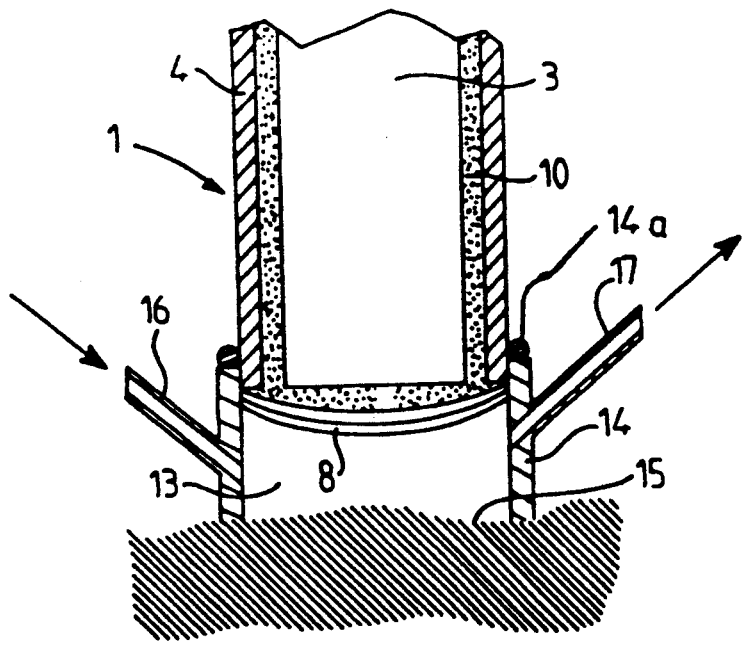

For measurement, the electrode obtained in this manner was combined with a thermostatted measuring cell (Radiometer D616), so as to comprise the biosensor as shown in previously described FIG. 2.

The enzymatic reaction occurring in accordance with the invention at the end of the Clark electrode was the following:

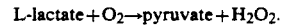

$$L\text{-lactate} + O_2 \rightarrow \text{pyruvate} + H_2O_2.$$

Figure 3:
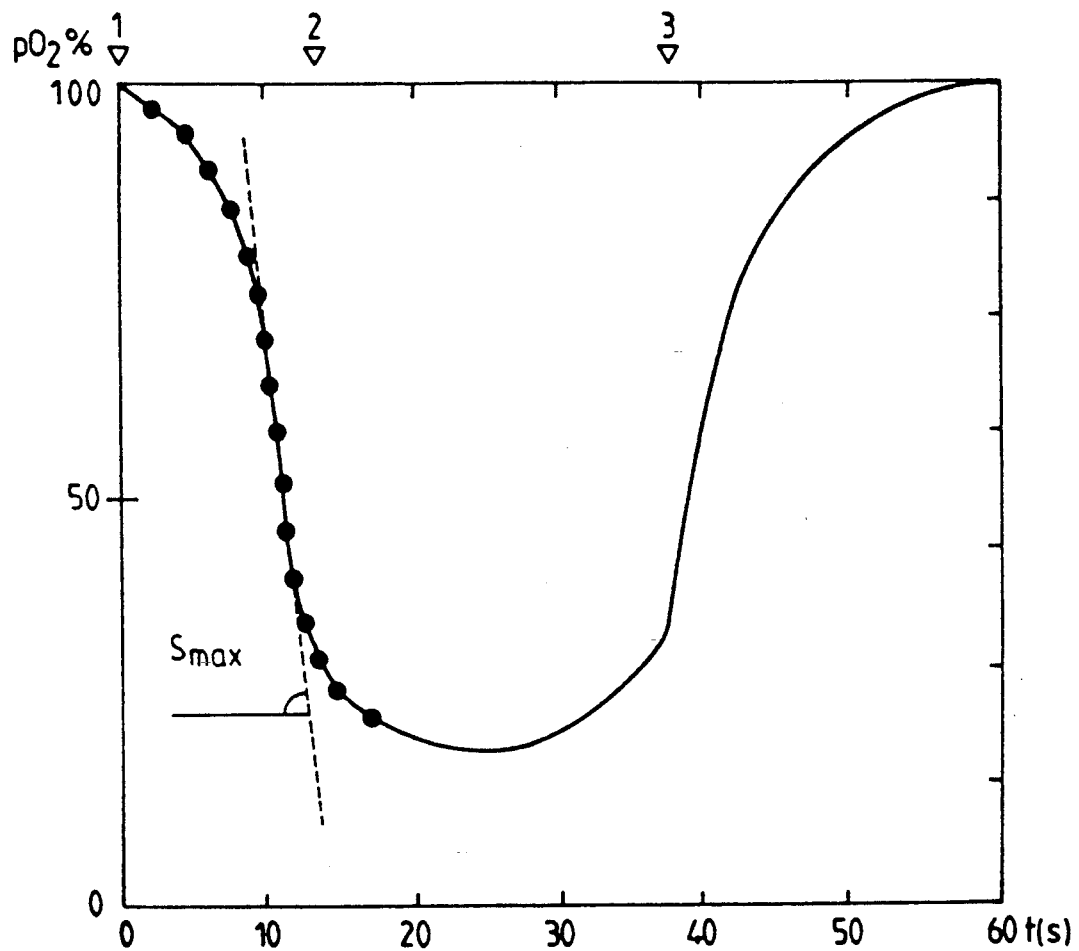
FIGS. 3 to 13 represent different curves obtained during measurements carried out, inter alia, to optimize said electrode.

For the calibration of the biosensor and the study of the same, the cell 13 was supplied with a continuous flow of an aqueous lactate solution with a known concentration. The calibratable data for these measurements during continuous flow was the Smax slope at the inflection point of the curve of the pO$_2$ signal (partial oxygen pressure) recorded by the electrode. FIG. 3 shows a typical curve obtained during a measuring cycle during continuous flow: the abscissa shows the time in seconds and the ordinate shows the partial oxygen pressure (pO$_2$) expressed as a percentage in relation to the initial pO$_2$ pressure of the buffer. In this measuring cycle, the L-lactate was added to the cell with the phosphate buffer 0.1 M, pH 7, at time (1). The cell was rinsed with the buffer at time (2). Air was added to the cell at time (3) to ensure again the 100% oxygen saturation of the membrane used. The mathematical processing of the signal is known (Kernevez et al., Biotech. Bioeng. 1983, 25, 845). The automatic processing of the signal, the fluidic circuit and the acquisition of the calibration curves were controlled by a microcomputer in a known manner.

The measuring cycle during continuous flow of the biosensor prepared as indicated above sequentially comprised the three phases corresponding to times (1) to (3) indicated above in reference to FIG. 3, it being understood that it began with the step of exposure to air of the membrane. The step of exposure to air was carried out so as to increase the oxygen concentration inside the active membrane, which then became twenty times greater than in water for the same partial oxygen pressure (Belgith, H. Doctoral Thesis, Compiegne University, 1985).

As can be seen below, for repetitive direct measurements on a same cutaneous area, the step of exposure to air is not performed for practical reasons.

The effective use of the biosensor in accordance with the invention was, in this example, carried out as follows. The biosensor, whose measuring cell had a volume of 100 μl for an application surface of 0.6 cm$^2$, was applied onto the skin. The phosphate buffer 0.1 M, pH 7.1, was injected at room temperature (21° C.) into the measuring cell using a peristaltic pump (Gilson Minipuls 3), providing a fill flow on the order of 1.2 ml/min. which was constant and perfectly reproducible. Once the cell was filled, the pump was stopped; the $pO_2$ value was recorded as a function of time (see curve on FIG. 12). Initially, the $pO_2$ had the value corresponding to air ($pO_2$ air). At time 0 the buffer was added (point Ao on the curve) the $pO_2$ value decreased to become stabilized at the value of the partial oxygen pressure in the buffer ($pO_2$ buffer). Then the buffer circulation pump was stopped at time $t_1$: $pO_2$ increased which translates into the balancing of the buffer temperature with the cutaneous temperature; however, since time 0, the enzymatic membrane began its action which tends to decrease the $pO_2$ value given by the electrode, with this action being masked by the above-defined phenomena. The $PO_2$ value therefore passed through a maximum $A_1$ resulting from two simultaneous antagonistic actions, with this maximum being reached for a time $t_2$. After this, $pO_2$ decreased due to the enzymatic action; however, this decrease was halted by a supply of oxygen from the buffer; at each instant, therefore, there was a balance; however, the lactate concentration in the measuring cell increased through diffusion of the lactate over time from the cutaneous covering and the curve obtained therefore translated a succession of stationary states. After a sufficient time, for example approximately 4 minutes, the buffer was recirculated: $pO_2$ decreased rapidly for a short instant, which translated the heterogeneousness of the medium in the measuring cell and then, after a minimum B, reincreased to return approximately to the value of the $pO_2$ in the measuring buffer.

Figure 12:
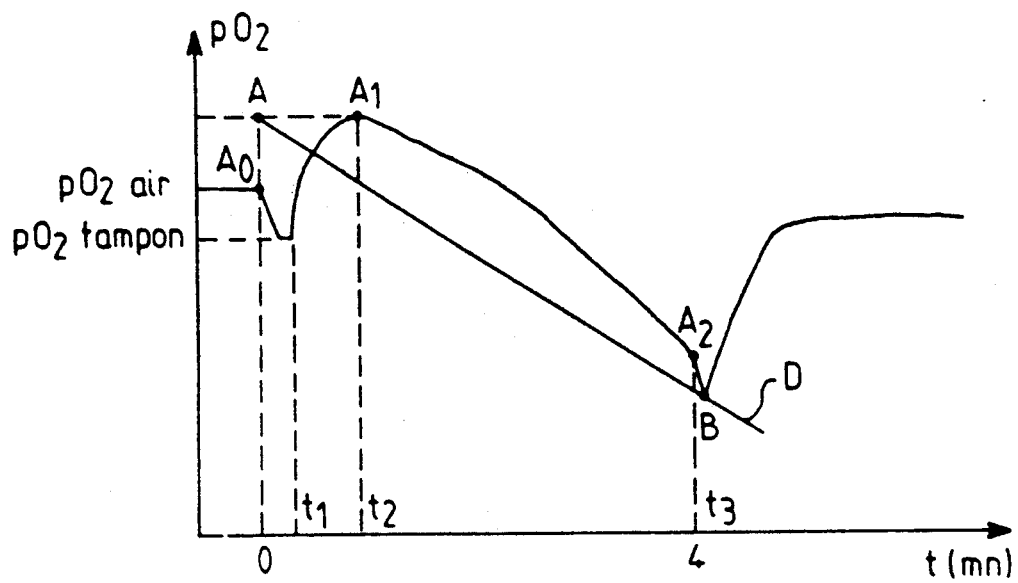

It has been noted that the most representative data of the amount of cutaneous lactate is the slope P of the straight line D which passes through the two points A and B of the graph of FIG. 12:
 point A:
 abscissa = time 0
 ordinate = value of the maximum $A_1$ at time $t_2$
 point B:
 minimum B reached by the curve after recirculation of the buffer.

The value P can be used to express the amount of lactate diffusing in nmoles/mn/cm$^2$ provided this is related to a standard carried out in stationary mode, that is at the plateau value of $pO_2$ obtained when the oxygen consumed by the enzymatic reaction is exactly compensated by the oxygen supplied by the measuring medium.

As indicated above, since each measurement is followed by a buffer circulation phase, several successive measuring cycles can be carried out on a same site.

Figure 13:
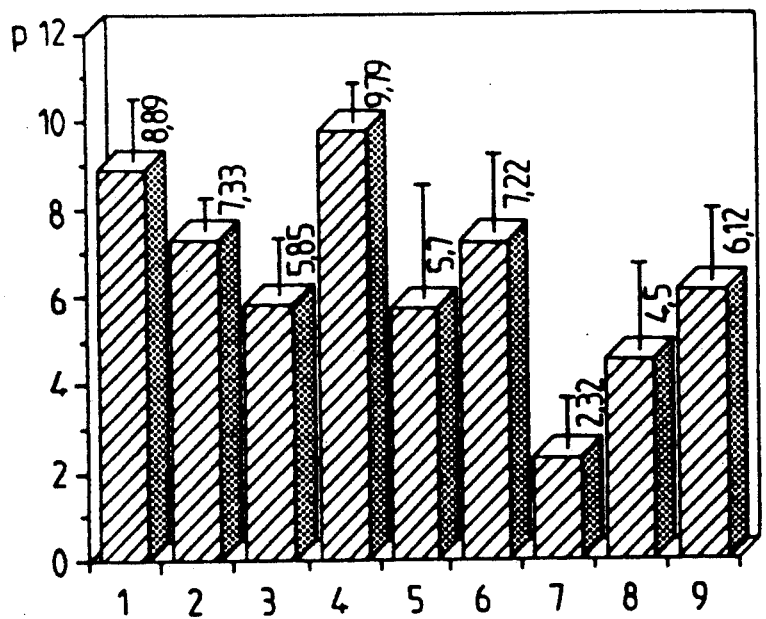

By way of indication, FIG. 13 gives the values obtained (slopes P) for measurements carried out on the forearms of nine individuals of the female sex. These values are cumulative values resulting from four measurements per individual (2 successive measurements for a same area on each forearm).

Given below are a certain number of indications which led to the development of the optimized biosensor, which is described above, and to its optimal use.

I. OPTIMIZATION OF THE BIOSENSOR

1) Optimization of the Enzyme Immobilization Steps

The good mechanical and biochemical stability of the active enzymatic membrane is the essential condition rendering possible the analytical use of the biosensor. This stability depends on certain physical, chemical or biochemical factors:

a) The enzyme concentration in the active membrane

Figure 4:
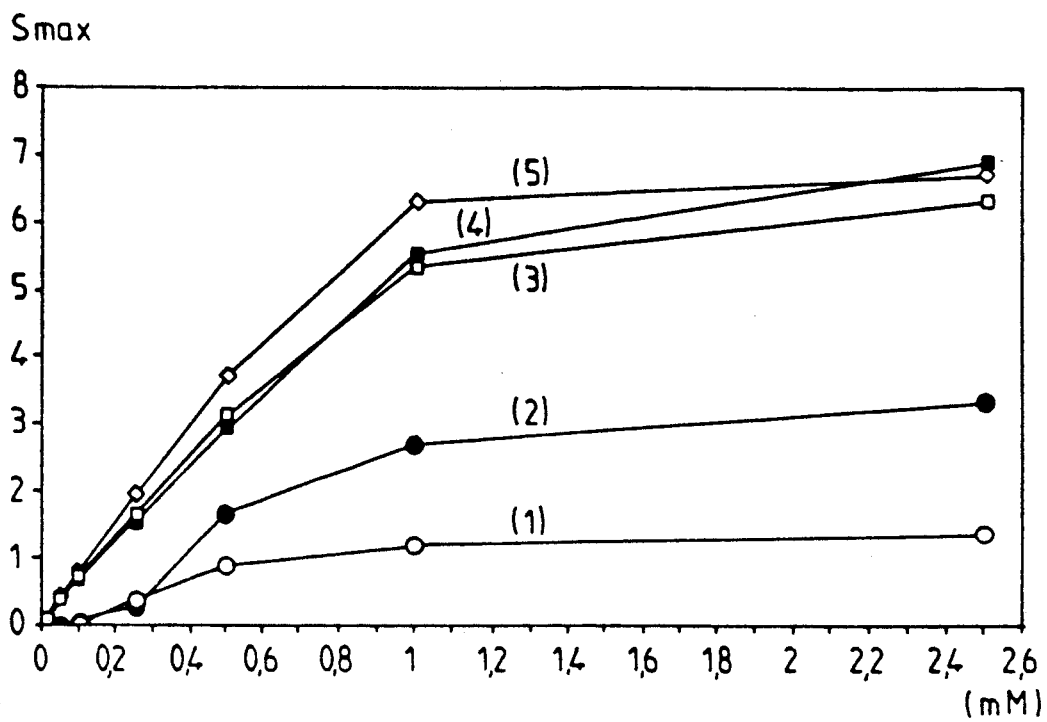

FIG. 4 of the attached drawings shows different calibration curves (1) to (5), which were prepared with membranes containing different concentrations of L-lactate oxydase under the following common conditions:

Phosphate buffer: 0.1 M, pH 7.1;
 Time of crosslinking using a 1.25% solution of glutaraldehyde (weight/volume): 3 minutes;
 Concentration of the gelatin solution: 5% (weight/volume);
 Temperature: 21° C.;
 Legend of FIG. 4
 Abscissa: concentration of L-lactate in Mm;
 Ordinate: Smax slope defined on the curve of FIG. 3;
 Quantity of L-lactate oxidase (expressed in IU for 35 cm$^2$ of gelatin film) for curves (1) to (5): 1; 4; 10; 20 and 30, respectively.

The results show that high enzyme concentrations (>4IU/35 cm$^2$) can be used to measure relatively low lactate concentrations (linearity response zone situated between $1 \times 10^{-5}$ and $1 \times 10^{-3}$ M). When the lactate concentration varies between 1 and 3 mM, membranes containing 4 IU must be used.

Moreover, with an excess of enzyme (>4 IU), the response of the electrode becomes independent of the amount of enzyme. This is related to two factors: the saturation of the protein membrane at active sites; and the increase of the enzymatic protein mass and therefore of the thickness of the membrane (an increase in enzymatic activity in the membrane cannot be obtained with a constant enzymatic protein mass).

The limiting factor of the electrode response then becomes the substrate diffusion coefficient. Such experimental conditions (enzyme saturation) can be used advantageously, providing electrodes with a more stable response, a small loss of enzymatic activity or a partial release of the enzyme having only a slight effect on the signal.

In view of these results, in the following studies and for each parameter studied, an enzyme concentration of 10 IU for 35 cm$^2$ was selected.

b) Crosslinking time using qlutaraldehyde

This step of preparation of the enzymatic membrane is very important, because the glutaraldehyde, which can block certain free amine groups of amino acids involved in the active site, is applied onto the protein film for a fixed period of time.

Figure 5:
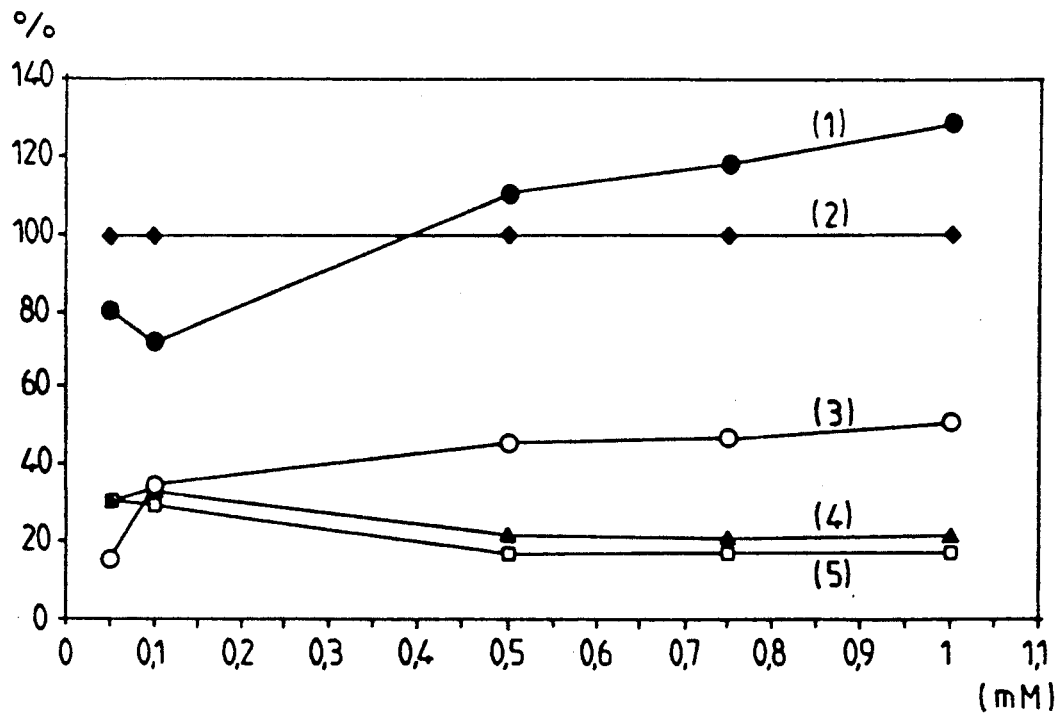

FIG. 5 of the attached drawings shows different response curves (1) to (5) of the L-lactate oxidase biosensor for different crosslinking times using an aqueous solution of 1.25% glutaraldehyde (weight/volume) (100% of the response for a crosslinking time of 3 minutes), under the following common conditions:

Phosphate buffer: 0.1 M, pH 7.1;
Concentration of the gelatin solution: 5% weight/volume);
Temperature: 21° C.;
Legend of FIG. 5
Abscissa: concentration of L-lactate (in mM);
ordinate: percentage of the response in relation to that obtained for a crosslinking time of 3 minutes;
Crosslinking time for curves (1) to (5): 1.5; 3; 5; 7.5 and 10 mn, respectively.

This figure shows that the highest biosensor responses were obtained for crosslinking times of 1.5 to 3 minutes. Higher crosslinking times cause a higher denaturation of the enzyme and a higher cohesion of the membrane, limiting the amount of lactate diffusion. These two factors lead to a decrease in the signal, which is proportional to the crosslinking time for contact times of over 3 minutes. The showing of best mechanical properties for a crosslinking time of 3 minutes in relation to 1.5 minutes led to the selection of that time for preparing membranes in the previously-described embodiment.

c) The gelatin concentration

Figure 6:
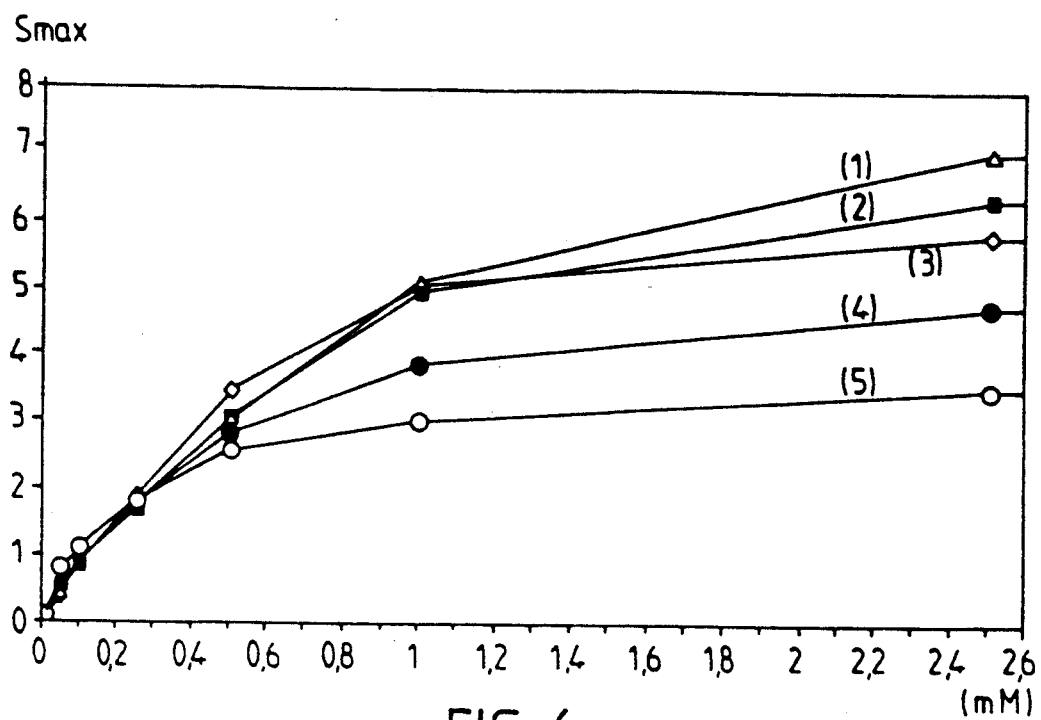

Membranes were tested containing the same amount of enzyme (10 IU for 35 cm$^2$) with variable amounts of gelatin (solutions from 3 to 7% for the preparation of membranes in accordance with the process given in the preceding example). FIG. 6 shows the calibration curves for the use of different percentages of gelatins [curves (1) to (5)], under the following common conditions:

Phosphate buffer: 0.1 M, pH 7.1;
Time of crosslinking using a 1.25% solution of glutaraldehyde (weight/volume): 3 minutes;
Temperature: 21° C.;
Legend of FIG. 6
Abscissa: concentration of L-lactate in mM;
ordinate: Smax slope (defined on FIG. 3)
Percentage of gelatin in the gelatin solutions used for curves (1) to (5): 3; 4; 5; 6 and 7, respectively.

Various factors must be considered firstly, the final enzymatic protein density decreases with the increase of the percentage of gelatin; therefore, theoretically, the protein film must be more active in the finer membranes;

secondly, since the thickness of the membrane increases when the gelatin concentration increases, the lactate diffusion coefficient and, consequently, the electrode response are modified;

thirdly, since the protective effect against the inactivating properties of the glutaraldehyde (crosslinking time equal to 3 minutes) increases in parallel to the percentage of gelatin, the catalytic activity is therefore best preserved in thicker films.

A compromise must therefore be found between these various factors. FIG. 6 shows that the best electrode response is obtained, for substrate concentrations of greater than 0.2 mM, with membraned having 5% gelatin.

The general recommendations for the preparation of enzyme electrodes in accordance with the invention are to use an enzyme having a specific activity which is as high as possible to ensure rapid kinetics in a membrane as fine as can be prepared to ensure the best rates of substrate diffusion. However, the optimization steps must be carried out for each new system and results, such as the mechanical resistance of the membrane, can play a part in the final choice of optimal conditions.

b 2) Optimization of the measuring conditions

Using membranes prepared under the optimal conditions determined above (10 IU for 35 cm$^2$; crosslinking time: 3 minutes; percentage of gelatin: 5%; and substrate concentration of 0.5 mM), the following were studied:

a) The effect of the molarity of the phosphate buffer

Figure 7:
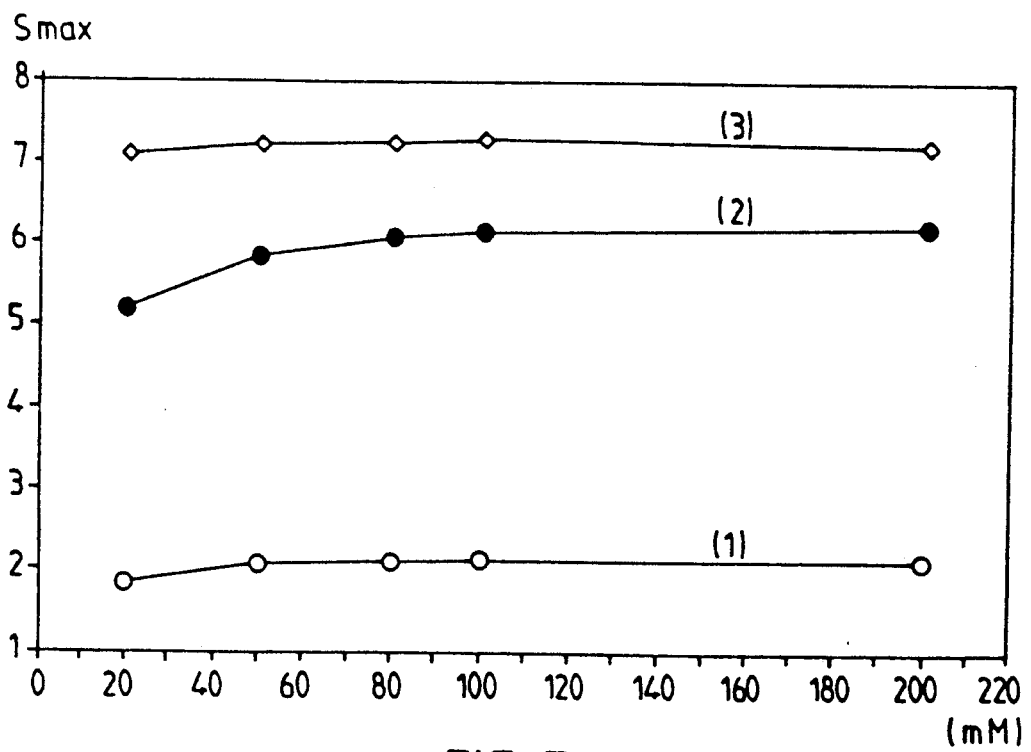

FIG. 7 represents the curves (1) to (3) giving the response of the biosensor in accordance with the invention as a function of the concentration of the phosphate buffer (pH 7.1) for three different membranes using variable amounts of enzyme under the following common conditions:

Crosslinking time using a solution of 1.25% glutaraldehyde (weight/volume): 3 minutes;
Concentration of the gelatin solution: 5% (weight/volume);
Temperature: 21° C.;
Concentration of L-lactate: 0.5 mM.
Legend of FIG. 7
Abscissa: concentration of the phosphate buffer (in mM);
Ordinate: Smax slope (defined on FIG. 3);
Amount of enzyme for (IU for 35 cm$^2$) for curves (1) to (3): 1; 4, and 10, respectively.

It is thus shown that the molarity of the buffer at the concentrations studied has only a slight effect on the response of the electrode.

Moreover, when the ionic strength of a phosphate buffer 0.1 M, pH 7.1, is increased by adding increasing amounts of NaCl (0.1 to 2.0 M), the electrode response does not vary (curve not shown). The length of the membrane rinsing step must, however, be increased and this probably in conjunction with an increase in the viscosity of the solution.

It is appropriate to note that the variations in ionic strength or of the pH of the buffer can take place, for example, during direct measurement on a saline concentration medium which is as variable as that of the stratum corneum. The above results show that such variations have only very little influence on the electrode response.

b) The effect of the pH of the measuring buffer on the electrode response

Figure 8:
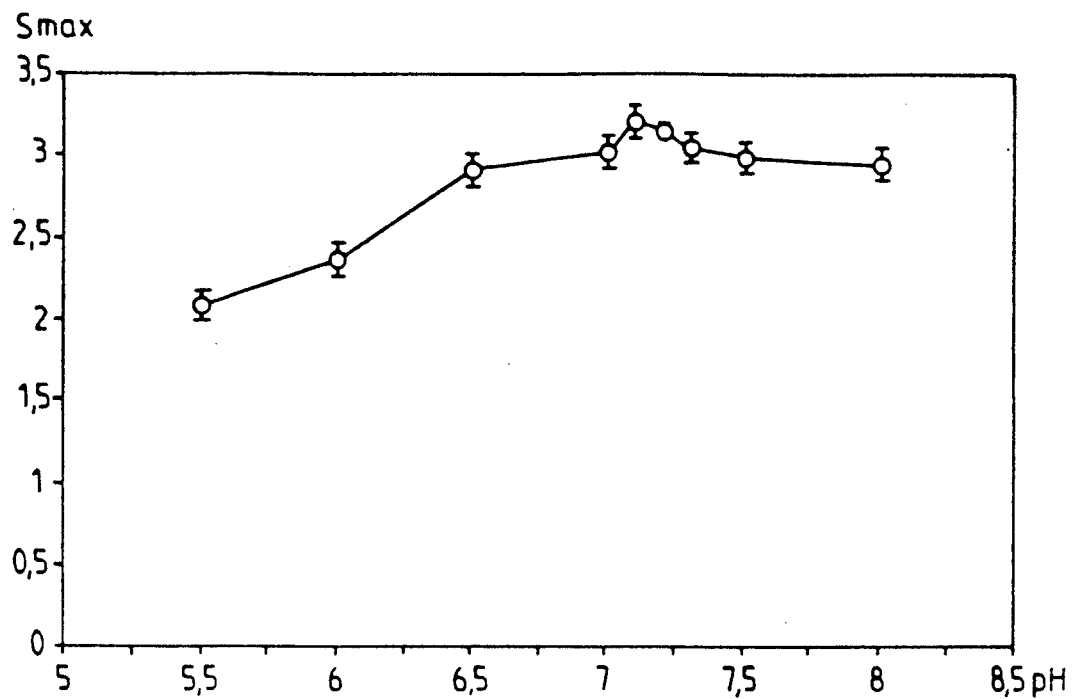

FIG. 8 shows the response of the biosensor (Smax slope value defined in FIG. 3) as a function of the pH, with each dot representing the average of four determinations, under the following common conditions:

10 UI membrane for 35 cm$^2$;
Phosphate buffer: 0.1 M;
Crosslinking time using a solution of 1.25% glutaraldehyde (weight/volume): 3 minutes;
Concentration of the gelatin solution: 5% (weight/volume);
Temperature: 21° C.;
Concentration of L-lactate: 0.5 mM.

It is thus shown that, when the pH varies between 6.5 and 8, no considerable change is noted in the electrode response. The response is maximum for a pH of 7.1 under the test conditions.

c) The effect of the temperature of the measuring medium

Figure 9:
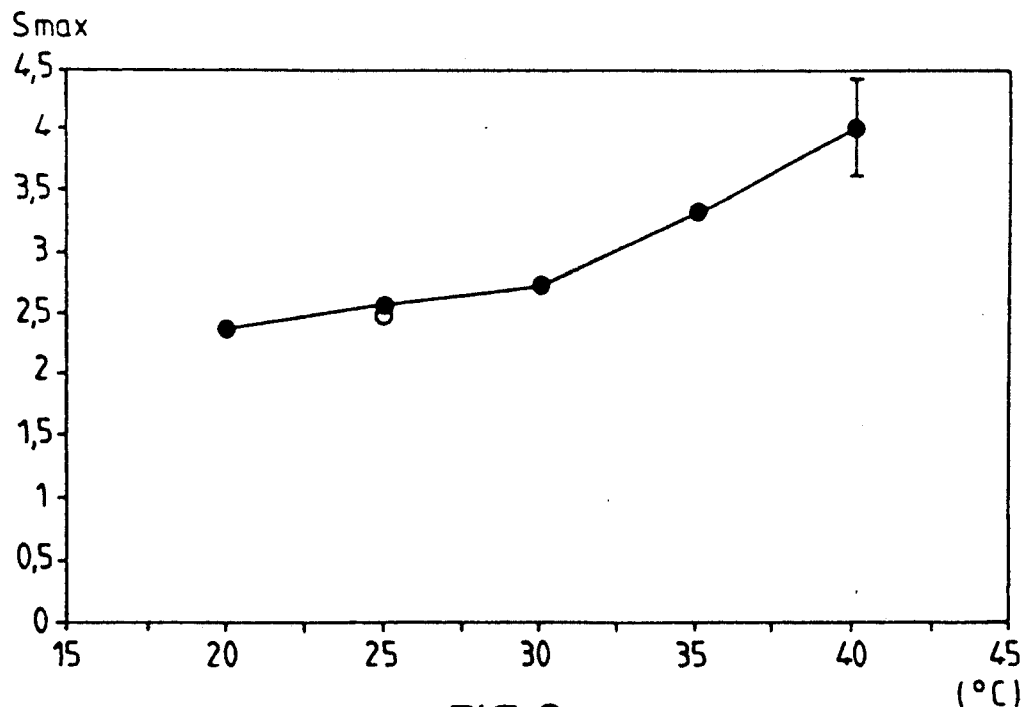

FIG. 9 shows the biosensor response (Smax slope value defined in FIG. 3) as a function of the temperature, with each black dot representing the average of four determinations, under the following common conditions:

10 UI membrane for 35 cm$^2$;
Phosphate buffer: 0.1 M, pH 7.1;
Crosslinking time using a solution of 1.25% glutaraldehyde (weight/volume): 3 minutes;
Concentration of the gelatin solution: 5% (weight/volume);
Concentration of L-lactate: 0.5 mM.

The reference (circled dot) constitutes a verification of the stability of the enzyme, under the above-identified conditions, at the end of a temperature test cycle going up to 50° C. and returning to 25° C. A high temperature increase up to 50° C. (time maintained at this temperature: approximately 15 minutes) did not cause a notable modification in the response of the electrode brought back to 25° C.

As shown in FIG. 9, increasing the temperature from 20° C. to 40° C. for a lactate concentration of 0.5 mM improves the response of the electrode. However, for temperatures above 35° C., the percentage of variation of the measurement becomes very high (greater than 10% at 40° C.), with this probably being related to the electrolyte degassing process. All the continuous flow experiments were therefore carried out at 21° C. This shows the important thermal and mechanical stability of the enzymatic membrane of the biosensor in accordance with the invention.

II. USE OF THE BIOSENSOR

1) Stability a) Stability under storage conditions

Figure 10:
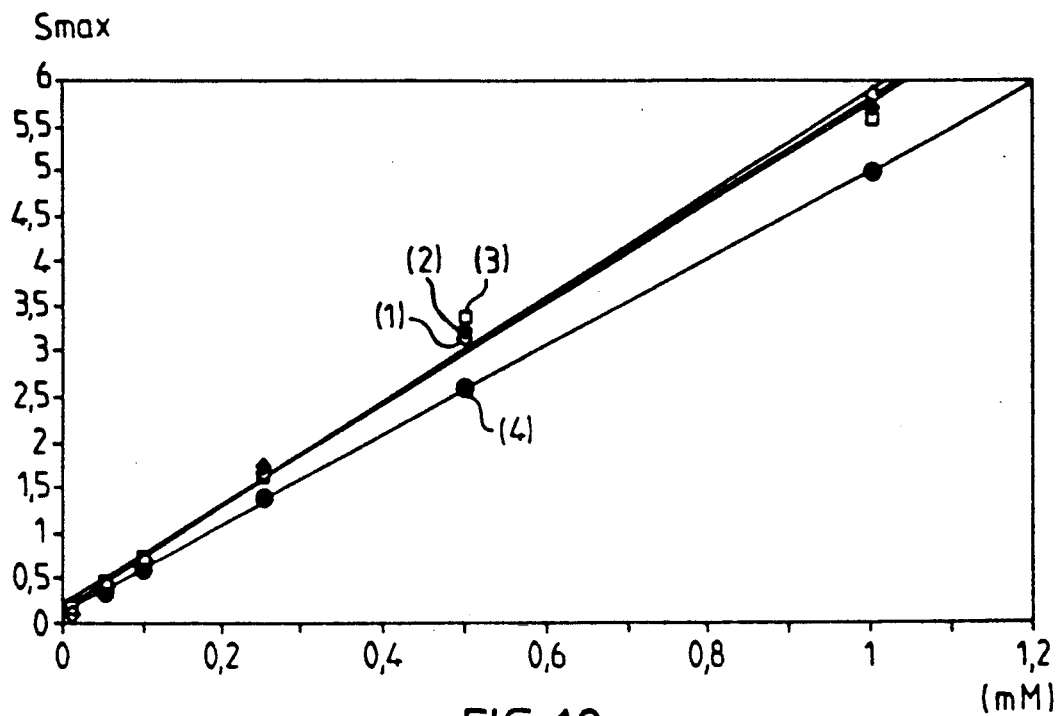

FIG. 10 illustrates the linearity zone response of the biosensor at various times after the preparation of the membrane.

Legend of FIG. 10
Abscissa: concentration of the L-lactate in mM;
Ordinate: Smax slope defined in FIG. 3;
Curves (1) to (4): 1; 9; 35; and 75 days, respectively, after the preparation of the membrane.

The enzymatic membranes were stored at 4° C. in the measuring buffer without sodium azide; no variation in the electrode response was noted during the first month. For up to 3 months of storage the detection limit and the linearity response zone were preserved and measurements could still be taken in a precise manner due to an appropriate calibration curve.

b) Stability during continuous operation

Figure 11:
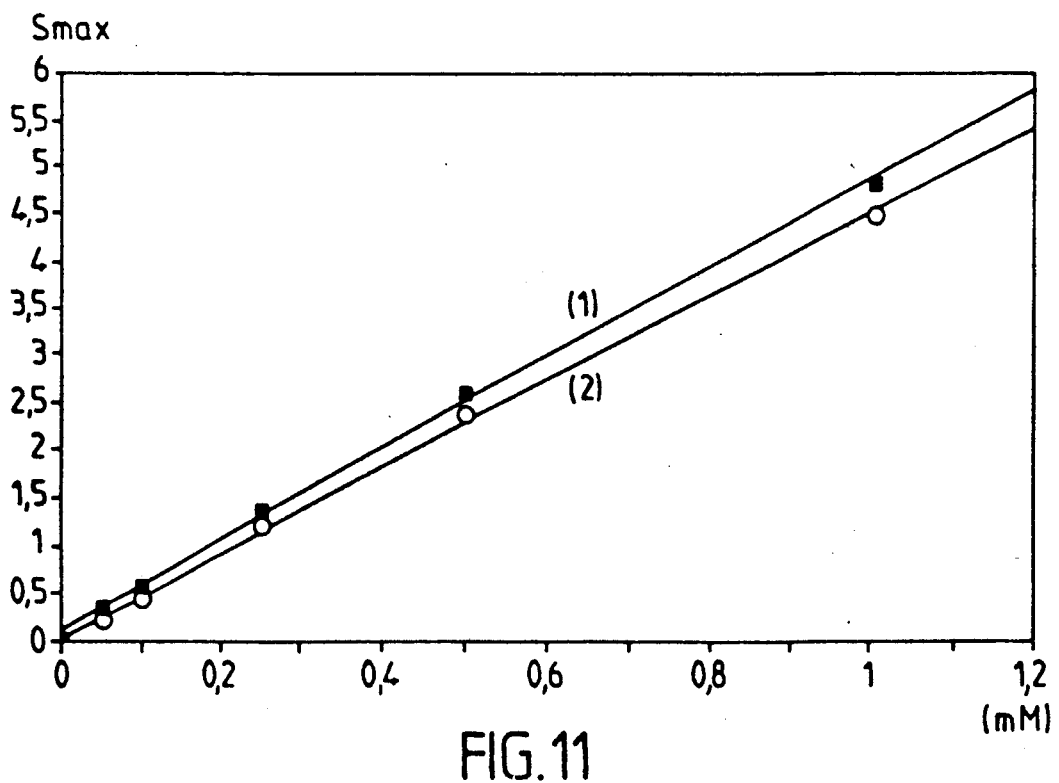

FIG. 11 illustrates the response, by linearity zone, of the biosensor after operation for 15 days.

Legend of FIG. 11
Abscissa: concentration of L-lactate in mM;
Ordinate: Smax slope defined in FIG. 3;
(1): reference calibration curve
(2): after 15 days.

The stability of the response of the biosensor was tested in continuous cycle with standard concentrations of L-lactate of 2 mM. Eight hundred measuring cycles (approximately 1 minute each) were able to be carried out without notable modification in the response (2 series of experiments). In the continuous flow system, the exceptional operational stability could in part be attributed to the fact that the contact time with the L-lactate was reduced to 10 seconds per cycle. Oxidases often have auto-inactivation kinetics, due to loss of cofactor (FAD), due to the $H_2O_2$ or due to the active species of oxygen produced during the enzymatic reaction. The auto-inactivation is all the more severe when the concentration of the two substrates is increased. In order to obtain maximum periods of stability, it is, therefore, interesting to limit the contact time with the L-lactate solution as much as possible.

C) Stability during discontinuous operations

The stability of the biosensor was tested for alternating periods of storage (4° C. in the phosphate buffer) and measurement (cutaneous measurements and in continuous flow at 21° C.). Even when the sensitivity decreased in a notable manner (after 15 days and after more than 500 measurements), the detection limit and the linearity were retained and measurements could still be carried out in a precise manner.

These results make the biosensor in accordance with the invention a system whose variations in sensitivity can be controlled by simple daily calibrations, thus ensuring the reliability of the results obtained.

2) Accuracy of the Measurements

The variability of the measurements carried out in continuous flow under the control of a micro-computer was less than 4% (perfect reproducibility of the conditions capable of influencing the measurement; constant injection pressure of the sample; perfectly reproducible cycle).

3) Specificity

The results obtained with the biosensor in accordance with the invention were compared with those obtained from samplings submitted to a lactate determination using liquid phase chromatography. A correlation coefficient of 0.999 was obtained which demonstrates the perfect operation of the biosensor in accordance with the invention and its specificity for the measurement of L-lactate without interference from the other compounds present on the cutaneous covering.

We claim:

1. A method for the direct measurement of at least one biochemical parameter of the skin, the method comprising the steps of:

providing a biosensor which comprises a measuring cell (13), a wall area of said measuring cell being composed of an enzymatic membrane (8) having an immobilized enzyme intended to catalyze the transformation of a cutaneous substrate, a means for circulating a liquid within the measuring cell (13) for placing in solution said cutaneous substrate to be measured, and a means for detecting a chemical or pressure change caused by said transformation, which is representative of the concentration of said cutaneous substrate to be measured, with said cutaneous substrate being brought into contact with said enzymatic membrane (8), said measuring cell (13) having an opening which is capable of being closed, during the measurement, by a cutaneous covering area (15);

applying said biosensor to a selected zone of said cutaneous covering area (15), such that said opening of said measuring cell (13) is closed by said zone of said cutaneous covering area (15).

filling said measuring cell (13) with a liquid capable of solubilizing said cutaneous substrate wherein said cutaneous substrate catalytically reacts with said immobilized enzyme in said enzymatic membrane, producing therein a measurable effect, after said step of filling said measuring cell, circulating the liquid for solubilization of said cutaneous substrate, and detecting and measuring said chemical or pressure change caused by the transformation of said cutaneous substrate due to the catalysis of the immobilized enzyme of the enzymatic membrane (8).

2. The method in accordance with claim 1, wherein measurement is repeated on said selected zone of said cutaneous covering area, without exposure of the enzymatic membrane (8) to air between two measurements of said selected zone of said cutaneous covering area.

3. The method in accordance with claim 1 wherein, said cutaneous substrate is a cutaneous lactate and said liquid is a buffer having a pH of between 6 and 8, wherein a recording of the variation in partial oxygen pressure $pO_2$ is measured as a function of time during non-circulation of the buffer in the measuring cell, wherein on the recording are defined point A having for abscissa injection of said buffer and for ordinate, a maximum value of $pO_2$, wherein a straight line D connecting A to a minimum point B of a curve resulting from said variation in partial oxygen pressure is defined, and wherein slope P of said straight line is measured for use as a representative amount of cutaneous lactate present in said skin.

4. The method in accordance with claim 3, further comprising the step of stopping the circulation of said buffer for a period of 3 to 6 minutes prior to measurement of the variation in partial oxygen pressure.

* * * * *